US006927389B2

(12) United States Patent
Curry et al.

(10) Patent No.: US 6,927,389 B2
(45) Date of Patent: Aug. 9, 2005

(54) BI-DIRECTIONAL SCANNER CONTROL SYSTEM

(75) Inventors: Bo U. Curry, Redwood City, CA (US); Jayati Ghosh, San Jose, CA (US); Kenneth L. Staton, San Carlos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 380 days.

(21) Appl. No.: 10/309,465

(22) Filed: Dec. 3, 2002

(65) Prior Publication Data

US 2004/0108447 A1 Jun. 10, 2004

(51) Int. Cl.[7] .............................. H01J 3/14; H01J 40/14; H01J 5/16
(52) U.S. Cl. ...................................... 250/234; 359/383
(58) Field of Search .............................. 250/234, 201.2, 250/559.29; 356/318; 359/383; 435/6, 7.1

(56) References Cited

U.S. PATENT DOCUMENTS

| | | | |
|---|---|---|---|
| 5,091,652 A | | 2/1992 | Mathies et al. |
| 5,260,578 A | | 11/1993 | Bliton et al. |
| 5,296,700 A | | 3/1994 | Kumagai |
| 5,324,633 A | | 6/1994 | Fodor et al. |
| 5,585,639 A | | 12/1996 | Dorsel et al. |
| 5,721,435 A | * | 2/1998 | Troll ..................... 250/559.29 |
| 5,760,951 A | | 6/1998 | Dixon et al. |
| 5,763,870 A | | 6/1998 | Sadler et al. |
| 6,078,390 A | | 6/2000 | Bengtsson |
| 6,084,991 A | | 7/2000 | Sampas |
| 6,222,664 B1 | | 4/2001 | Dorsel |
| 6,284,465 B1 | | 9/2001 | Wolber |
| 6,320,196 B1 | | 11/2001 | Dorsel et al. |
| 6,335,934 B1 | | 1/2002 | Sakurai et al. |
| 6,371,370 B2 | | 4/2002 | Sadler et al. |
| 6,400,487 B1 | * | 6/2002 | Harris et al. ............. 250/201.2 |
| 6,406,849 B1 | | 6/2002 | Dorsel et al. |

OTHER PUBLICATIONS

Qingbo Li et al., entitled "Fully Automated Multiplexed Capillary Systems for DNA Sample Analysis," DOE Human Genome Program, Contactor–Grantee Workshop VIII, Feb. 27–Mar. 2, 2000 Santa Fe, NM.

Agilent G2565AA Microarray Scanner System with SureScan Technology, User Manual, pp. 1–100.

* cited by examiner

*Primary Examiner*—Thanh X. Luu
*Assistant Examiner*—Seung C. Sohn

(57) ABSTRACT

Optical scanner system approaches are described in which novel focusing approaches are provided. A control algorithm accounts for geometric variation of successive scans in opposite directions across a microarray slide or substrate in order to provide optimized focus. The feedback approach taught may involve PI or PID terms. In either type of control approach, a projected slope of the slide is calculated and followed back and forth outside a scan region of the array in exiting and entering fully adaptive focusing zones, respectively. During turn-around, the system may track a setpoint between the periods of following the extrapolated slope. Also provided are methods of using the subject system in a biopolymer array based application, including genomic and proteomic applications.

20 Claims, 3 Drawing Sheets

BI-DIRECTIONAL SCANNER CONTROL SYSTEM

FIELD OF THE INVENTION

This invention relates to biopolymer array optical scanners and, more particularly, to servomechanism focus control elements involved in bi-directional routines.

BACKGROUND OF THE INVENTION

Pharmaceutical, biotechnology, or genomics companies use DNA analysis systems for target identification and drug screening in pharmaceutical drug discovery. In many of these systems, biomolecules (e.g., DNA, RNA, cDNA, proteins) labeled with various dyes bind to chips that offer different molecular probe counterparts for binding in different locations of the chip. A scanner is then used to read the fluorescence of these resultant surface bound molecules under illumination with suitable (most often laser) light. The scanner acts like a large field fluorescence microscope in which the fluorescent pattern caused by binding of labeled molecules is scanned on the chip. In particular, a laser induced fluorescence scanner provides for analyzing large numbers of different target molecules of interest, e.g., genes/mutations/alleles, in a biological sample.

The scanning equipment typically used for the evaluation of arrays includes a scanning fluorometer. A number of different types of such devices are commercially available from different sources, such as Axon Instruments in Union City, Calif. and Perkin Elmer of Wellesly, Mass. Analysis of the data, (i.e., collection, reconstruction of image, comparison and interpretation of data) is performed with associated computer systems and commercially available software, such as GenePix by Axon Instruments, QuantArray by Perkin Elmer or Feature Extraction by Agilent of Palo Alto, Calif.

In such scanning devices, a laser light source generates a—most often collimated—beam. The collimated beam sequentially illuminates small surface regions of known location on an array substrate. The resulting fluorescence signals from the surface regions are collected either confocally (employing the same lens used to focus the laser light onto the array) and/or off-axis (using a separate lens positioned to one side of the lens used to focus the laser onto the array). The collected signals are then transmitted through appropriate spectral filters to an optical detector. A recording device, such as a computer memory, records the detected signals and builds up a raster scan file of intensities as a function of position, or time as it relates to the position. Such intensities, as a function of position, are typically referred to in the art as "pixels" or "pixel values."

In performing scans, a typical approach is to zigzag across a microarray slide or substrate obtaining data in a raster fashion. In doing so, it has been appreciated that very slight variation in the tilt or angle of a slide to be scanned, or variation in the planarity of the slide itself, must be accounted for in order to achieve acceptable focus and accurately obtain data on successive features.

For this purpose, known systems actuate a scanning lens assembly or the cradle/caddy carrying a slide by servomechanism(s) to bring features into focus by varying the distance between the items (in an effort to maintain a constant distance between the features being scanned and the optics). Known feedback logic controllers are used to accomplish this goal.

Two common types of electronic feedback controllers are Proportional-Integral (PI) and Proportional-Integral-Derivative (PID) controllers. The implementation of each may vary widely. Tuning and custom design of the same are well within the abilities of those with ordinary skill in the art.

The tuning required to make a selected control system suitable for a given application involves scaling the contribution to the control output of each component of the controller selected. The proportional component(s) of either type of controller operates to direct corrective action to a control element based on the present state of a given process relative to a desired setpoint. Integral component(s) operate by directing control action based on the sum of previous errors in the process. The error sum tends toward zero (and thus a desired state for a given process) as negative error conditions subtract from a positive error total or vice versa due to corrective action taken. Derivative components in a PID controller direct corrective action in response to a change in slope or sign of a measured error condition. As the derivative of a measured value is taken, this term is,keyed to rate of change of a process. Implementations of derivative control features include use in making larger or stepwise corrections as well as damping out system oscillations.

In electronic controllers as described, the measure of a given corrective effect in relation to the corrective input is understood in terms of control element gain. The controller's bias represents the control effort required to maintain the process at its setpoint absent external loading of the system.

With this understanding of the relevant controller types in mind, certain considerations in array scanning should be appreciated as background to the present invention. Namely, in typical array scanner systems, a lens is scanned back-and-forth across a slide or substrate, while a control algorithm attempts to hold focus by maintaining the distance between a lens and slide despite asymmetries present in the system. Without the teaching of the present invention, however, if the slide being scanned is steeply tilted or bowed with respect to the lens (i.e., the left side of the slide is nearer the lens than the right side, or vice versa), the inherent delays of an applicable PI or PID control algorithm cause the actual slide position to lag behind its setpoint/in-focus position. The integral term of the PI or PID control equation attempts to make up for this lag by, in effect, anticipating that the recently observed slope will continue and acting accordingly.

Generally, in a PID controller, $$V_{out}(t) = k_p e(t) + k_I I(t) + k_d D(t) \quad [1]$$

where $V_{out}(t)$ is the servo control voltage output at time step t, e(t) is the position error measured at time t, I(t) is the running sum of e(t), from t=0 until t, D(t) is the derivative of e(t) and $k_p$, $k_I$, and $k_d$ are tuning parameters. As one might suspect, in a PI system, there is no derivative term. In either type of system, additional terms may be included to further refine matters or provide additional functionality. Other related control equations are well known in the art as well.

During scanning of a sloped surface (i.e., a surface with a distance from the focused lens that increases or decreases substantially monotonically as the scan progresses), the l(t) term in equation [1] (the "integral" term—discussed below in terms of "I" alone in connection with the present invention) will grow until it reaches a value which corrects for the amount the error changes between the time it is measured and the time the control voltage takes effect.

When the scanner reverses direction, the sign of the slope that the integral term compensates for reverses. Since the integral term continues to add to its running sum, it will eventually adapt to the new tilt direction, and the controller will again control without error. However, in known systems, for a brief period at the start of the reversed scan line (the time until the integral term has time to adapt), the system will not be able to correct for the control loop lag.

This situation usually causes noticeable focus errors for the first few millimeters of each scan line. Typically, focus is undershot, at least partly because the integral term has not had sufficient time to "grow" adapting to the new conditions in the opposite scan direction. After undercompensating for focus, the typical result is overshooting focus as the control loop compensates for the observed error in the negative. The focus error causes a dip in the signal intensity in the scanned image at the beginning of the scan line. This sudden change in the signal intensity adversely affects the uniformity specifications of the scanner.

In instances where fully adaptive focus control is feasible (meaning that where significant borders or edge portions are provided around a scan area of a slide that are situated across from the lens assembly during the full motion of the system and the system is allowed to adapt to changing slope as it turns around), the system would be in focus upon returning to the region of interest. However, it is common practice to maximize array sizing/placement on a slide or substrate, leaving no room for purely adaptive control to provide accurate focus.

Accordingly, systems have been developed, such as described in U.S. patent application Ser. No. 10/087,220, entitled "Bi-Directional Scanner Control System," filed Feb. 28, 2001 (hereinafter the "'200 Application") that control to or maintain focus at a desired setpoint once leaving an active scan region of a slide corresponding to where array features are to be provided. Despite the marked improvement offered by that system over previous approaches, upon returning to the scan area after completion of scanning a line and turning around, another sort of focus error is introduced. Namely, mechanical/electromechanical delays inherent to moving components against inertial loads make the system unable to—respond instantly to conditions (such as slide tilt and/or curvature) requiring focus adjustment, even in response to a signal that is otherwise adequate to set focus. Accordingly, while the system in the '220 Application takes steps to avoid issues with the control loop integral term, it still sometimes under compensates for focus and then overcompensates in a like manner in instances where the scanner's physical parameters prohibit accurately tracking the slide/array surface upon reentering an active scan region.

The present invention offers a further improved focus control approach. Control algorithm integral terms are accounted for in a manner resembling the approach in the '220 Application where they are artificially set based on the state of a preceding scan line. However, the additional transient focus errors inherent in the referenced invention are accounted for. As such, the present invention offers expanded utility in dealing with more extreme situations. The approach is suitable for more demanding applications where slide tilt and/or curvature varies greatly. Yet, it is applicable in less extreme scanning applications as well. As such, the present invention meets the continuing need for improved data acquisition.

SUMMARY OF THE INVENTION

The present invention concerns methods related to maintaining focus on features in scanning arrays, especially biopolymer arrays, when scanning in a raster fashion. After leaving the active scan region of an array, the focus control system of the invention continues to track, for a finite distance, a slope projected for the line scan as if it were to continue. After reversing direction, the focus control mechanism follows the projected slope in that direction in order to transition smoothly into the active scan region. The temporal or spatial region in which the focus system tracks the projected or extrapolated slope may be referred to as the "extrapolation period." Between forward and reverse extrapolation periods, sufficient time or space may be left so that, during turn-around from one direction to the other, the focus system maintains a set position—preferably one coincident with the focal position set at the end of the extrapolation period in the forward direction.

Such methodology is preferably implemented using a PID controller, though a PI controller may sometimes be employed. The present invention includes the subject methodology, programming defining the same including such algorithms and/or equations as applied to the scanning solution, hardware configured to run according to the methodology and results or data produced according to the teachings of the present invention.

BRIEF DESCRIPTION OF THE DRAWINGS

Each of the figures diagrammatically illustrates aspects of the invention. To facilitate understanding, the same reference numerals have been used (where practical) to designate similar elements that are common to the figures.

DEFINITIONS

Figure 1:
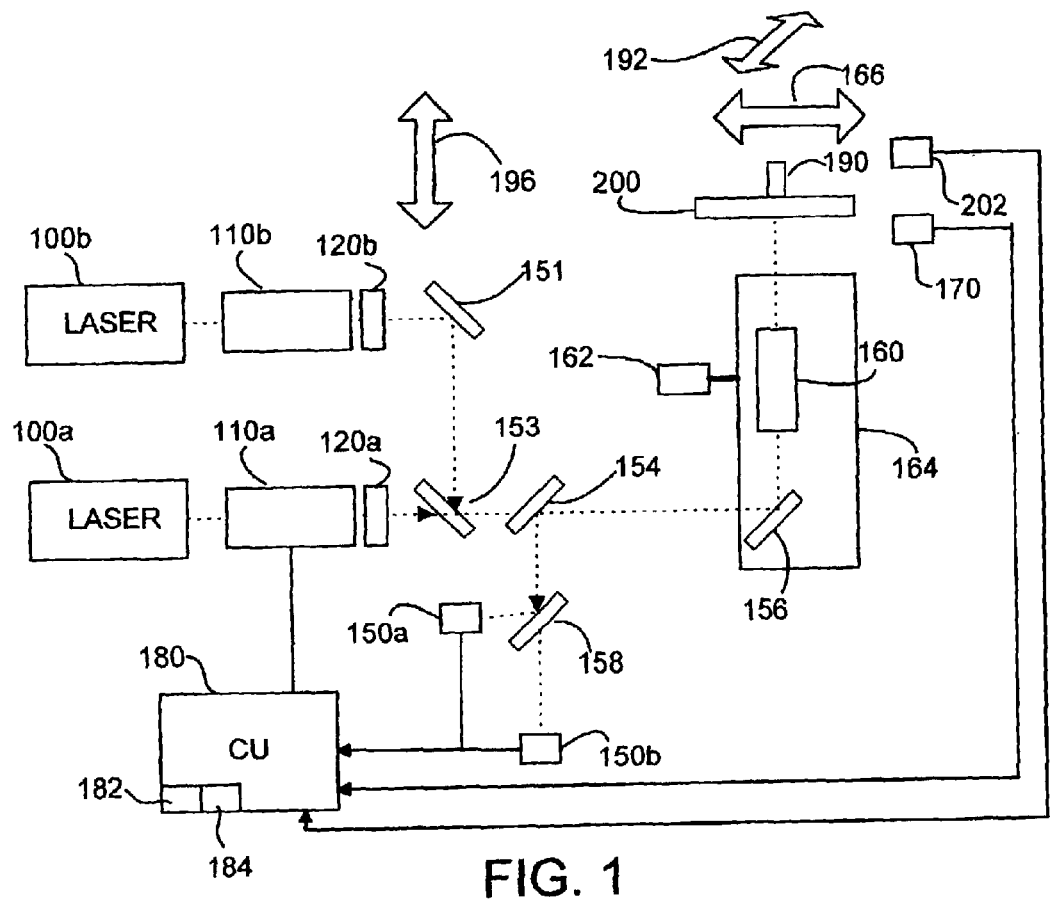
FIG. 1 schematically illustrates an optical scanner as may be used in the present invention.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" a polymer of one or more types of repeating units. Biopolymer are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer/polymer) of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups)

An "array," includes any two-dimensional or substantially two-dimensional (as well as a three-dimensional) arrangement of addressable regions bearing a particular chemical moiety or moieties (e.g., biopolymers such as polynucleotide sequences (nucleic acids), polypeptides (e.g., proteins), etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand, more ten thousand features, or even more than one hundred thousand features, in an area of less than 20 cm$^2$ or even less than 10 cm$^2$. For example, features may have widths (that is, diameter, for a round spot) in the range from a 10 $\mu$m to 1.0 cm. In other embodiments each feature may have a width in the range of 1.0 $\mu$m to 1.0 mm, usually 5.0 $\mu$m to 500 $\mu$m, and more usually 10 $\mu$m to 200 $\mu$m. Non-round features may have area ranges equivalent to that of circular features with the foregoing width (diameter) ranges. At least some, or all,of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m , usually more than 4 mm and less than 600 mm , more usually less than 400 mm; a width of more than 4 mm and less than 1 m, usually more than 500 mm and more usually less than 400 mm; and a thickness of more than 0.01 mm and less than 5.0 mm , usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 file Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. Nos. 5,599,695, 5,753,788, and 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other; (thus, either one could be an unknown mixture of polynucleotides to be evaluated by binding with the other).

A "scan, region" refers to a contiguous (e.g., rectangular) area in which the array spots or features of interest, as defined above, are found. The scan region is that portion of the total area illuminated from which the resulting fluorescence, chemiluminescence, or other optical detection techniques is detected and recorded. For the purposes of this invention, the scan region includes the entire area of the slide scanned in each pass of the lens, between the first feature of interest, and the last feature of interest, even if there exist intervening areas that lack features of interest. The scan region does not, however, include "border regions" or "borders" of the array substrate/slide adjacent slide edges and adjacent to but not including or covered by array features. Generally, any borders around the scan region are less than about 5–15 mm and can be as little as 1 mm, or even smaller, if the mechanical design of the slide holder permits it. It is often desirable to lay down features as close to the edge of the substrate as possible so as to maximize the number of different probes that may be displayed on a given surface area. As such, in many array configurations, the width of a border, if present, between the scanned arrays and the slide edge does not exceed about 20 mm, usually does not exceed about 10 mm and more usually does not exceed about 5 mm.

"Lens position" refers to the relative distance between the lens or optical objective(s) of a scanner and a caddy carrying a slide and/or the slide or array itself.

An "array layout" refers to one or more characteristics of the features, such as feature positioning on the substrate, one or more feature dimensions, and an indication of a moiety at a given location. "Hybridizing" and "binding", with respect to polynucleotides; are used interchangeably.

By "remote location," is meant a location other than the location at which the array is present and hybridization occurs. For example, a remote location could be another location (e.g., office, lab, etc:) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system, are suitable for use in the present invention. The data storage means may comprise any manufacture comprising a recording of the present information as described above, or a memory access means that can access To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION

In describing the invention in greater detail than provided in the Summary and as informed by the Background and Definitions provided above, the subject program or process aspects of the invention are first described. Next, an exemplary optical scanner is described, including invention-specific hardware aspects of the same. This discussion is followed by a description of methods of using scanners in accordance with the present invention, kits for use in the invention and an exemplary implementation.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be, drafted to exclude any optional element. As such, this statement is intended to serve as antecedent basis for use of such exclusive terminology as "solely," "only" and the like in connection with the recitation of claim elements, or use of a "negative" limitation.

METHODOLOGY/PROGRAMMING

As summarized above, the present invention involves software control for a scanner or optical imaging system, preferably a biopolymer array optical scanner, and associated methodology for maintaining optical focus for array features when scanning in a raster fashion. The solution offered herein is suited for scanning array slides or substrates that present even at a large angle and/or with appreciable curvature. For example, slides with linear slopes of over 8 um/mm, and with bowed centers greater than 200 urn over a span of 100 mm, have been successfully held in focus by means of the invention.

Programming embodying the methodology may be loaded onto an optical scanner, or the scanner may be preprogrammed to run with the same. The programming can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording:of the present database information.

As noted, the present invention is preferably implemented with a PID control system. Yet, it should improve the focus accuracy of any control system that includes an integral term, whether or not it also includes a derivative term, or other terms.

Regardless, in the present invention, the integral term of the PI or PID control algorithm can be broken down into a part which functions to anticipate the slope of a substrate or slide being scanned (whether resultant from slide tilt or curvature of the same), and another part which is required to hold lens or housing position to maintain focal length in the absence of slide tilt (i.e., it accounts for system bias such as the bearings in the assembly, or other asymmetries in the mechanism such as those associated with nonlinear servo control voltage). The latter, quantifiable term is referred to as $I_{resting}$. The former part is referred to as $I_{slope}$, but it cannot be isolated or directly measured.

Scanning in the present invention is preformed on arrays/slides for which the slope changes little from one scan line to an adjacent scan line (but is observed to have an opposite sign in due to movement in the opposite direction during scanning). However, slide slope may vary significantly over a given scan line, though it will vary only gradually along a scan line (i.e., it will be substantially continuous and/or predictable without a step function or significant alteration or change/discontinuity).

Under such conditions, the following equations are applied in the present invention:

$$I_{forward} = I_{resting} + I_{slope} \quad [2]$$

$$I_{reverse} = I_{resting} - I_{slope} \quad [3]$$

where $I_{forward}$ is the integral term required to hold focus to a slide with a positive tilt and $I_{reverse}$ is the integral term required to hold focus when the slide is tilted in the reverse direction (actually, the slide is tilted in the same direction in space, but is scanned in the reverse direction). Rearranging equation [2]:

$$I_{slope} = I_{forward} - I_{resting}. \quad [4]$$

Substituting equation[4]into equation [3]:

$$I_{reverse} = I_{resting} - (I_{forward} - I_{resting}) \text{ or } 2(I_{resting}) - I_{forward}. \quad [5]$$

In carrying out the present invention, when scanning in raster fashion the above equations are utilized to anticipate $I_{reverse}$ by setting it to the supposed equivalent value (i.e., $2(I_{resting}) - I_{forward}$). The timing associated with the application of equation 5 may be observed in connection with FIG. 4A.

This figure depicts the primary operational approach of the present invention. Particularly, from the period of time indicated as 0–40 ms, scanning is being accomplished in the scan region of the slide. Curved line 300 represents lens position/the tracking of focus—as indicated by focal position (x)—to the actual contour of the slide being scanned. The contour of the smooth parabolic form of the slide that was scanned may be noted. The variation or focus error relative to the contour of the slide is indicated in ten-fold scale as line 302.

At a point "B" active adaptation of the focus assembly to the contour of the slide is terminated. However, the focus assembly continues to operate. For a brief period or distance up to point A, the focus servo mechanism(s) follows an extrapolated or projected slope E, based on the previously observed slope trend that is preferably measured just before point B. Producing such a projection of slope is easily accomplished with the ordinary level of one with skill in the art.

At point A, a setpoint is established in accordance with the position of point A where it is attempted to hold lens position. Further, $I_{forward}$ is recorded. Departure of the actual lens position 306 from the setpoint position 304 as tracking and scanner turn around roughly at the midpoint of line 304 may be observed. The oscillation introduced due to the step function at point A in setting a new tracking position is dramatic at first but dies out substantially upon return to a point A', adjacent to point A with the scanner traveling in the opposite direction. The length of time or distance "S" between point A and A' for tracking the setpoint is preferably such that the integral term of the control algorithm is able to adapt and hold, or substantially hold, lens position to the setpoint indicated by line 304. Once stabilized, the value of the integral error is recorded as $I_{resting}$. It will be advantageous in many situations to record $I_{resting}$ at point A' since this is the farthest point for which the algorithm is given time to adapt to a constant setpoint position.

Upon reaching point A', the system lens position is set to track extrapolated slope E' with $I_{reverse}$ set artificially to equal $2(I_{resting}) - I_{forward}$ This continues to point B', where the algorithm is used to track the actual slope of the slide in the active scan region resumes, in the opposite direction along line 300'.

When the assumptions noted above are valid, as may be observed the focus error 302' achieved in tracking the slide is comparable to that previously observed. Importantly, little or no evidence is apparent of the under compensation/over compensation pairing noted above that may occur as a result of electromechanical elements unable to respond quickly to changes in slope. The problem is cleanly avoided because the focus servo mechanism controlling lens position is already traveling and tracking a slope that closely approximates the actual slope of the slide upon return to the scan region, following turn-around.

As with the setpoint tracking period S, the length of the extrapolation period E/E') may be varied. Longer tracking distance or time better allows the-system to adapt to the slope change from the setpoint to the extrapolated value. The required tracking distance depends on the response time of the servo system, which can be measured from the time required to stabilize after a step change to the setpoint. The system shown in FIG. 3 has a response time of about 2 ms, so a settling time of 5 ms produces excellent results. Control systems with higher gain and/or looser tolerances may require less tracking time, and systems with lower gain may require more. Longer periods/distances than required are of little utility and will merely increase scanner cycle time.

While $I_{resting}$ is preferably measured during turn-around of the lens or array cradle assembly (especially at point A') to provide the best approximation available, this value may be determined or set otherwise. Furthermore, in instances where $I_{resting}$ would be sufficiently low (even negligible), the term may be dropped from equations [2] and [3] thereby producing a simplified approach where these equations are rearranged so:

$$I_{reverse} = -I_{forward} \qquad [6]$$

Note, however, that in most cases superior results will be obtained if $I_{resting}$ is not discarded. In accordance with such an approach where $I_{resting}$ is to be ignored, it may be desirable to omit setpoint tracking period S. Space limitations prohibiting lengthy turn-around regimes may prompt such action.

Whatever the action is that precedes actively tracking slide position in the active scan region, the servo focus control system (i.e. autofocus system) takes measurements and proceeds as is typical based on the control algorithm selected until the end of the next scan row, where the entire process repeats, running in the opposite direction. It is noted that in a preferred embodiment of the system, the EOMs turn the lasers off while the scanner reverses direction, thus avoiding both autofocus instability and detector damage. Laser life may also be extended in this manner.

Also, it is noted that the invention may be configured for use in, alternately, 1) a fully adaptable mode, 2) a mode as described above, and 3) a mode as described in the '220 Application. Where an array with sufficiently large borders B are present, conventional PI, PID or a related manner of servo focus control may be utilized to good effect. However, even in instances where the control approach can be selected between a known approach and that of the present invention, it may be desired to set-up the system to use the method of the present invention as its default program to handle the more common array situation.

Regardless, as evidenced below it should be appreciated that the present invention functions with superb results. Therefore, little advantage (if any) would be offered by a system that can toggle between settings. Accordingly, it is most preferred to program a scanning system solely with the subject program methodology.

As noted variously, the scanner used is preferably one suited for scanning biopolymer arrays. Any number of scanners will be suitable for such purposes, especially those noted herein.

Optical Scanners

Also provided by the subject invention are biopolymer array optical scanners that are programmed as described above. Any biopolymer optical scanner or device may be provided to include the above programming. Representative optical scanners of interest include those described in U.S. Pat. Nos.: 5,585,639; 5,760,951; 5,763,870; 6,084,991; 6,222,664; 6,284,465; 6,329,196; 6,371,370 and 6,406,849—the disclosures of which are herein incorporated by reference. An exemplary optical scanner as may be used in the present invention is shown in FIG. 1.

A light system provides sample excitation light from a source such as a laser 100. The light passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light beam exiting from the attenuator.

The light from both lasers 100a, 100b is transmitted through a dichroic beam splitter 154, reflected off fully reflecting mirror 156 and focused onto either an array (not shown) mounted on holder 200, or a calibration member (not shown), whichever is at a reading position, using optical components in beam focuser 160. Light emitted (in particular, fluorescence) at two different wavelengths (e.g., green and red light) from features 16, in response to the interrogating light, is imaged using the same optics in focuser/scanner 160, and is reflected off mirrors 156 and 154. The two different wavelengths are separated by a further dichroic mirror 158 and are passed to respective detectors 150a and 150b.

More optical components (not shown) may be used between the dichroic and each detector 150a, 150b, splitter 154 or mirror 158 (such as lenses, pinholes, filters, fibers, etc.) and each detector 150a, 150b may be of various different types (e.g., a photo-multiplier tube (PMT) or a CCD or an avalanche photodiode (APD)). All of the optical components through which light emitted from an array or calibration member in response to the illuminating laser light, passes to detectors 150a, 150b, together with those detectors, form a detection system. A scan system causes the illuminating region in the form of a light spot from each laser 100a, 100b, and a detecting region of each detector 150a, 150b (which detecting region will form a pixel in the detected image), to be scanned across multiple regions of an array or an array package mounted on holder 200.

However the detector(s) 150 are configured, the scanned regions for an array will include at least its multiple probe features. The scanning system is typically a line by line scanner, scanning the interrogating light in a line across an array as described below when at the reading position, in a direction of arrow(s) 166, then moving ("transitioning") interrogating light in a direction into/out of the paper as depicted by arrow(s) 192 as viewed in FIG. 1 to a position at an end of a next line, and repeating the line scanning and transitioning until the entire array has been scanned.

This scanning feature is accomplished by providing a housing 164 containing mirror 156 and focuser 160, which housing 164 can be moved along a line of pixels (i.e., from left to right or the reverse as viewed in FIG. 1) by a transporter 162. The second direction 192 of scanning (line transitioning) can be provided by second transporter which may include a motor and belt (not shown) to move caddy 200 along, one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The scanner of FIG. 1 may further include a reader (not shown) to read an identifier from an array package. Such an identifier may be in the form of a bar code that can be read by a suitable bar code reader.

Of course, the movements 166 and 192 may be accomplished by actuating holder 200 or housing 164 alone. Still further, the movement roles described for each element above may be swapped.

An autofocus detector 170 is generally provided to sense any offset (variation in slope) between different regions of array 12 when in the reading position, and a determined position of the focal plane of the detection system. The autofocus system includes detector 170, processor 180, and a motorized or servo-controlled adjuster 190 to move holder 200 in the direction of arrow 196 to establish lens position correct focus for the system. The detector may directly detect a partial reflection from another beamsplitter (not shown) (e.g., between splitters 153 and 154). In addition, a second position detector 202, also feeding back to the CU, preferably measures the absolute position (i.e., relative to the apparatus) of the servo-controlled adjuster 190). As above with respect to movements 166 and 192, it should be observed that focus servo control movement indicated by arrows(s) 196 (i.e., controlling lens position) may occur in connection with housing 164 or focusing optics 160 instead of the holder.

Further details regarding suitable chemical array autofocus hardware is described in pending U.S. patent application Ser. No. 09/415,184 for "Apparatus, And Method For Autofocus" by Dorsel, et al., filed Oct. 7, 1999, as well as European publication EP 1091229 published Apr. 11, 2001 to the same title and inventors—the disclosures of which are herein incorporated by reference. Details as to the manner of focusing such hardware, other suitable hardware, is the subject of the methodology above and as provided in the Example below.

In any case, array orientation and configuration is of little consequence in this context (though it may be in other situations) since focus can be set to probe features either directly, or looking through a transparent substrate medium if the array is inverted for scanning.

Controller 180 of the apparatus is connected to receive signals from detectors 150a, 150b, these different signals corresponding to different "channels," i.e., signals which result at each of the multiple detected wavelengths from emitted light for each scanned region of an array when at the reading position mounted in holder 200. Controller 180 also receives the signal from autofocus offset detector 170 and absolute servo position detector 202, and provides the control signal to EOM 110, and controls the scan system. Controller 180 may also analyze, store, and/or output data relating to emitted signals received from detectors 150a, 150b in a known manner.

Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network, possibly a wireless network) with a remote site (such as a database at which information relating to array package 30 may be stored in association with the identification 40).

The controller is suitably programmed to execute all of the steps required by it during operation of the apparatus. Alternatively, controller 180 may be any hardware or hardware/software combination which can execute those steps.

Utility

The subject biopolymer optical scanners find use in a variety applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as an isotropic or radioactive or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids (or other molecules) that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos.: 5,143,854; 5,288,644; 5,324, 633; 5,432,049; 5,470,710; 5,492,806; 5,503,980; 5,510, 270; 5,525,464; 5,547,839; 5,580,732; 5,661,028; 5,800, 992—the disclosures of which are herein incorporated by reference.

Where the arrays are arrays of polypeptide binding agents, e.g., protein arrays, specific applications of interest include analyte detection/proteomics applications, including those described in U.S. Pat. Nos.: 4,591,570; 5,171,695; 5,436, 170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

Figure 2:
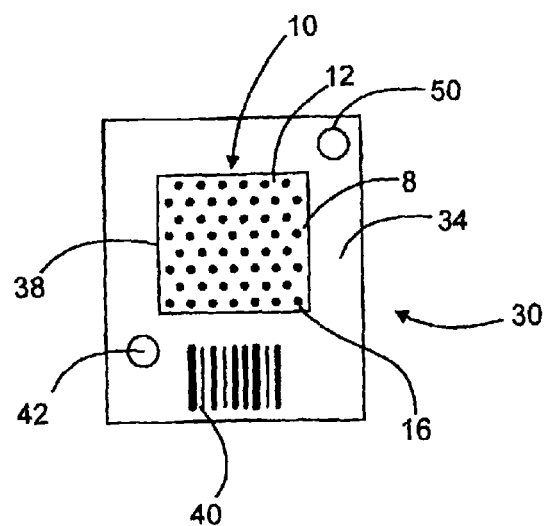
FIG. 2 is a front view of a packaged array that may be used in connection with scanners according to the present invention.

An exemplary array is presented in FIG. 2. Array 10 carries multiple probe features 16 disposed across a surface of the substrate 12. The substrate is preferably in the form of a contiguous, substantially planar substrate made of transparent material to facilitate data acquisition scanning there through. Alternatively, the substrate could be scanned from the side which carries features 16. Features 16 (not to scale) are shown disposed in a pattern which defines the array. The extent of the pattern defines a scan region 8. (Difference between 8 and 10 not clear from drawing.)

Array 10 may be set within a housing 34 to provide an array package 30. In which case, substrate 10 is sealed (such as by the use of a suitable adhesive) to housing 34 around a margin 38. Housing 34 is configured such that housing 34 and substrate 12, define a chamber into which features 16 of the array face. This chamber is accessible through resilient septa 42, 50 which define normally closed ports of the chamber. An identifier 40, possibly in the form of a bar code, may be affixed to housing 34. The composition of the probe features and material(s) used to produce elements of the array package may vary, but may be as typical in the art.

In using an array in connection with a programmed scanner according to the present invention, the array will typically be exposed to a sample (such as a fluorescently labeled analyte, e.g., protein containing sample) and the array will then be read. Reading of the array may be accomplished by illuminating the array and reading the location and intensity of resulting fluorescence at each feature of the array to detect any binding complexes on the surface of the array. It is further noted that aspects of the invention may be applicable to a variety of optical scanners including those that detect chemiluminescent or electroluminescent labels.

In any case, results from reading an array may be raw results (such as fluorescence intensity readings for each feature in one or more color channels) or may be processed results such as obtained by applying saturation factors to the readings, rejecting a reading for a feature which is above or below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote, location for further evaluation and/or use. Any convenient telecommunications means may be employed for transmitting the data, e.g., facsimile, modem, Internet, etc. Alternatively, or in addition, the data representing array results may be stored on a computer-readable medium of any variety such as noted above or otherwise. Retaining such information may be useful for any of a variety of reasons as will be appreciated by those with skill in the art.

Kits

Kits for use in connection with the subject invention may also be provided. Such kits preferably include at least a computer readable medium including instructions and programming embodying or adapted to direct the functionality as discussed above. The instructions may include software installation or setup directions to program an otherwise ordinary scanner so to function as described. The instructions may include directions for directing the scanner to perform as desired. Preferably, the instructions include both types of information.

Providing the software and instructions as a kit may serve a number of purposes. The combination may be packaged and purchased as a means of upgrading an existing scanner. The full program or some portion of it (preferably at least such code as defining the subject methodology—alone or in combination with the code already available) may be provided as an upgrade patch. Alternately, the combination may be provided in connection with a new scanner in which the software is preloaded on the same. In which case, the instructions may serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc., including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Of course, some form of access security or identification protocol may be used to limit access to those entitled to use the subject invention. As with the instructions, the means for obtaining the instructions and/or programming is generally recorded on a suitable recording medium.

EXAMPLE

The following examples are offered by way of illustration and not by way of limitation. In connection with an Agilent model G2505 B scanner running software according to the present invention and that according to the invention in the '220 Application, the scan profiles in FIGS. 3A and 3B were, respectively, produced. In each case, a PID type controller was run according to the following tuned equation:

$$V_{out}(t)=k_p e(t)+k_I I(t)+k_d D(t) \quad [1]$$

where $V_{out}(t)$ is the servo control voltage output at time step t to actuate focus control motion 196 (in volts), e(t) is the position error measured at time t (in $\mu$m), I(t) is the running sum of e(t), from t=0 until t (in $\mu$m-seconds), D(t) is the derivative of e(t) (in $\mu$m/sec), and $k_p$, $k_i$, and $k_d$ are tuning parameters, where $k_p$=0.04V/$\mu$m, $k_i$=6 V/$\mu$m/sec, and $k_d$=−2×10$^{-5}$ V-sec/$\mu$m. Though they may differ greatly depending on the various mechanical and electrical properties specific to a system, the values of these tuning parameters and such other terms as may be used are easily derived and implemented using standard control system tuning techniques. The scanner lens assembly used was set to a focal distance of +5$\mu$m (relative to an arbitrary zero) and scans of the same slide were made at 1 m/sec, so one ms on the time axis represents 1 mm of distance along the slide.

Figure 3A:
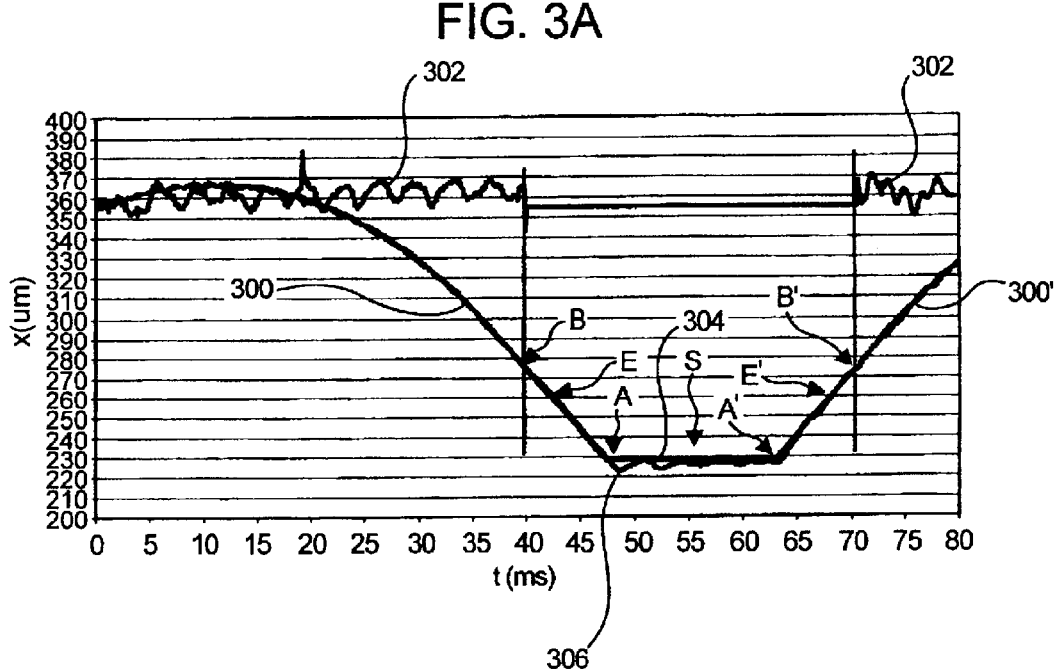
FIG. 3A shows a scan of an array slide or substrate using techniques according to the present invention.

The various elements of FIG. 3A have been discussed above. As may be observed, focus error upon entering the scan region and performing line scan 300' is minimal—if any discernable error over the system noise is present.

Figure 3B:
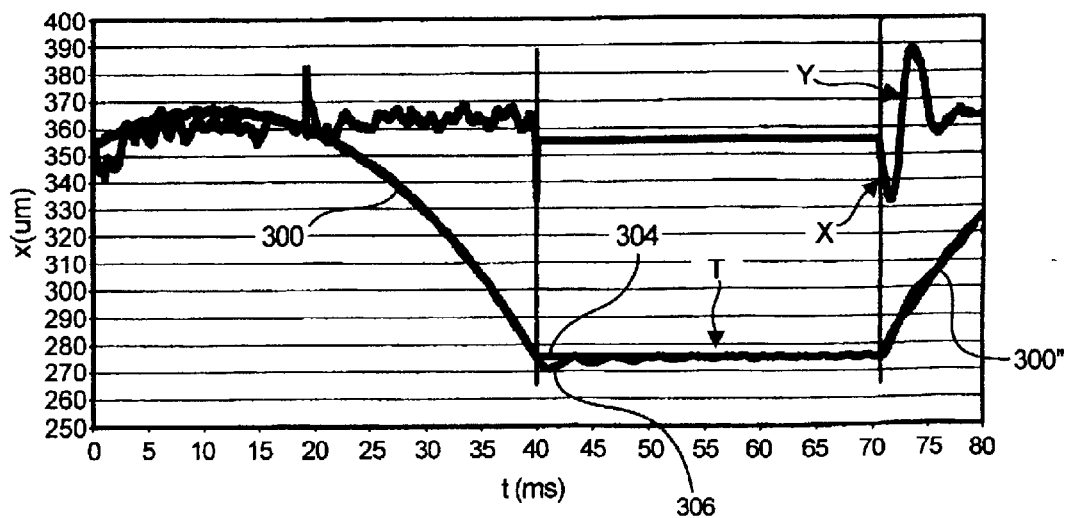
FIG. 3B shows a scan of the same item conducted using the technique described in the '220 Application noted above.

By way of comparison, the results in FIG. 3B produced according to the teachings of the '220 Application present quite noticeable transient focus error(s). In scanning in the scan region along line 300, results comparable to those in FIG. 3A are produced. However, in exiting the turnaround region "T" after the system controls to a setpoint coincident with the end of the scan region, a large undercompensation-based focus error "X," followed by an overcompensation based focus error "Y" observed. After roughly 5 ms the control algorithm adapts. Yet, such dramatic focus error(s) significantly affects the quality of focus attained by the, system presented in FIG. 3B at the beginning of each subsequent scan line in scan line 300". The errors resultant from changing step-wise from a set control point along line 304 to the parabolic slide roughly introduces roughly a 3-fold error due to inadequacy of the focus system servo/voice coil response. As may be seen by the comparative results, the present invention largely avoids the problem altogether.

Figure 4A:
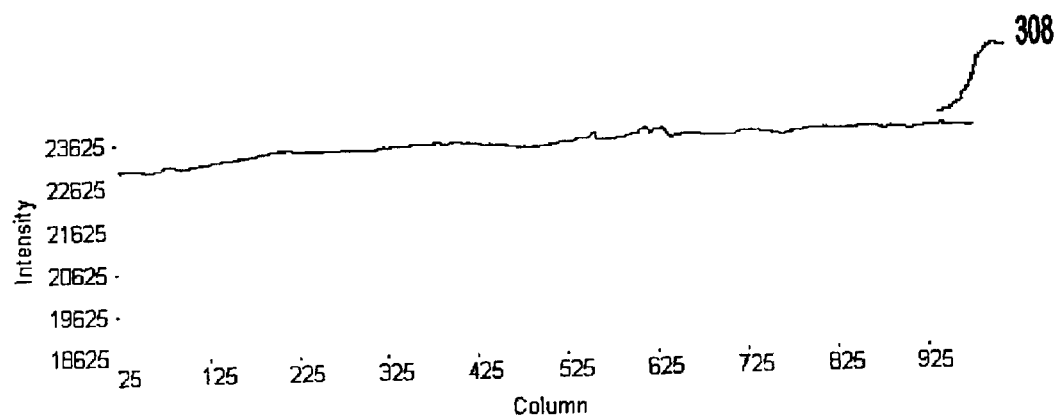
FIG. 4A shows the average signal intensity over all the scanned rows of one particular array, using techniques according to the present invention.
Figure 4B:
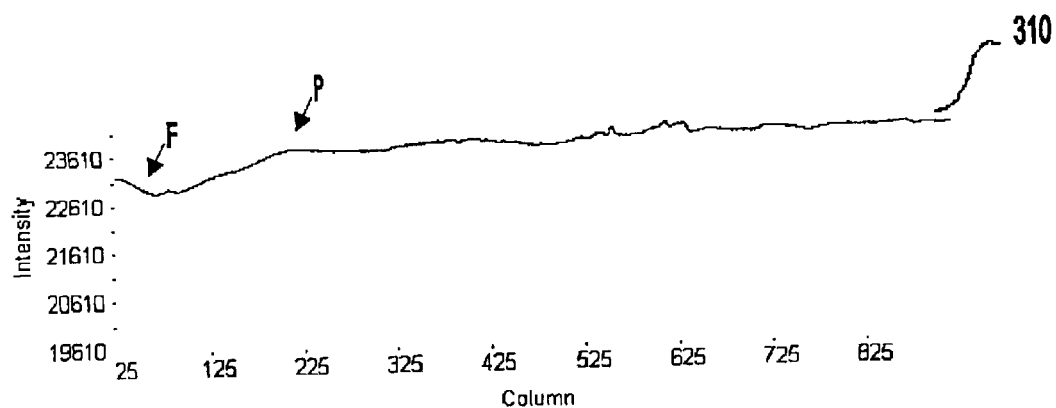
FIG. 4B shows the average intensity of the same conducted using the technique described in the '220 Application noted above.

Likewise, the present invention helps avoid inconsistency associated with scanned signal intensity that, as noted above, can adversely affect the uniformity specifications of the scanner. FIG. 4A shows a signal intensity 308 averaged over all the scanned rows of a particular array determined using a preferred approach according to the present invention; FIG. 4B shows the average signal intensity 310 of the same array conducted according to the technique described in the '220 Application noted above. In each instance, the scan data is represented in terms the average signal intensity of points aligned in columns of the various array rows scanned. The low numbered columns are those first scanned upon turn-around and reentry to the scan region.

What may be observed in comparing FIGS. 4A and 4B is that the focus error introduced in the '220 system produces a significant initial drop in the signal intensity. This focus error is denoted as "F" FIG. 4B The drop is followed by a relatively steep climb that levels-out at plateau point "P" values comparable to those present in FIG. 4A, where significantly less signal intensity drop or no such error is present.

Though the invention has been described in reference to certain examples, optionally incorporating various features, the invention is not to be limited to that specifically described. It is to be, understood that the breadth of the present invention is to be limited only by the literal or equitable scope of the following It is evident from the above discussion that the above described invention provides an effective and readily applicable way to improve the precision and extend the lifetime of optical scanners. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of scanning an array, said method comprising:

providing an optical scanner system comprising a processor and a scanning lens assembly;

providing an array comprising a substrate and a plurality of array features in a scan region;

scanning a first row with said lens assembly, utilizing an adaptive control algorithm to maintain focus of said lens assembly in said scan region by accounting for a slope of said substrate;

calculating a projected lens position based on extrapolation of said preceding substrate slope for an extrapolation period beyond said scan region;

controlling the position of said lens assembly to said projected lens position;

reversing scan direction to scan a second row, continuing to control the position of said lens assembly to said projected lens position until returning to said scan region; and resuming said adaptive control algorithm to maintain focus.

2. The method of claim 1, wherein a position of said lens assembly is held substantially constant relative to a caddy carrying said array from a termination of said extrapolation period to a start of maintaining focus along said projected slope in the reverse direction.

3. The method of claim 2, further comprising calculating an $I_{forward}$ term and an $I_{resting}$ term, wherein two times the value of said $I_{resting}$ term is added to said $I_{forward}$ term at a start of scanning said second row.

4. The method of claim 1 wherein the first and second scanned rows are adjacent one another.

5. The method of claim 1, wherein motion of a caddy carrying said array sets said lens position.

6. The method of claim 1, wherein said adaptive control algorithm is a PI algorithm.

7. The method of claim 1, wherein said adaptive control algorithm is a PID algorithm.

8. The method of claim 1, carried out in reading a biopolymer array.

9. The method of claim 8, wherein biopolymer on the bipolymer array comprises polypeptides or nucleic acids.

10. An optical scanner system comprising:

a processor and a lens assembly positioned opposite an array caddy; and a plurality of servo mechanisms to control a relative position of said lens assembly and said caddy in three axes;

wherein said processor is adapted to control lens position for sequential opposite-direction scans on array features situated on an array substrate to be carried by said caddy by tracking a slope of said substrate with an adaptive algorithm, calculating a projected slope beyond a scan region, controlling lens position to the projected slope in a first direction and then in a reverse direction, and again tracking a slope of said substrate with said adaptive algorithm.

11. The system of claim 10, wherein at least one servo mechanism controlling said caddy manipulates said lens position.

12. The system of claim 10, wherein said adaptive algorithm is a PI type adaptive algorithm.

13. The system of claim 10, wherein said adaptive algorithm is a PID type adaptive algorithm.

14. The system of claim 10, wherein said system is further adapted to hold a substantially constant lens position between following said projected slope in opposite direction scans.

15. The system of claim 10, further comprising a biopolymer array.

16. A method of scanning an array, said method comprising:

providing an optical scanner system comprising a processor and a scanning lens assembly;

providing an array comprising a substrate and a plurality of array features in a scan region;

scanning a first row with said lens assembly, utilizing an adaptive control algorithm to maintain focus of said lens assembly in said scan region by accounting for a slope of said substrate;

calculating a projected focus position based on extrapolation of said preceding substrate slope for an extrapolation period beyond said scan region;

reversing scan direction to scan a second row;

controlling the focus of said lens assembly following reversal based at least in part on the projected focus position; and resuming said adaptive control algorithm in the scan region to maintain focus.

17. The method of claim 16 wherein the focus of said lens assembly is maintained at the projected focus position until returning to said scan region.

18. The method of claim 17 wherein said adaptive control algorithm is resumed upon returning to the scan region.

19. The method of claim 16 wherein a projected focus position is calculated based on extrapolation of said preceding substrate slope for an extrapolation period beyond an edge of the substrate.

20. The method of claim 16 wherein the first and second scanned rows are adjacent one another.

* * * * *